United States Patent
Cui et al.

(10) Patent No.: US 12,304,947 B2
(45) Date of Patent: May 20, 2025

(54) RECOMBINANT ANTIBODY AGAINST HUMAN CARDIAC TROPONIN I

(71) Applicant: FAPON BIOTECH INC., Shenzhen (CN)

(72) Inventors: Peng Cui, Dongguan (CN); Zhiqiang He, Dongguan (CN); Yuan Meng, Dongguan (CN); Dongmei Zhong, Dongguan (CN); Hui You, Dongguan (CN); Lingyun Fan, Dongguan (CN)

(73) Assignee: Fapon Biotech Inc., Shenzhen (CN)

( * ) Notice: Subject to any disclaimer, the term of this patent is extended or adjusted under 35 U.S.C. 154(b) by 25 days.

(21) Appl. No.: 17/284,234

(22) PCT Filed: Sep. 27, 2019

(86) PCT No.: PCT/CN2019/108682
§ 371 (c)(1),
(2) Date: Apr. 9, 2021

(87) PCT Pub. No.: WO2020/073832
PCT Pub. Date: Apr. 16, 2020

(65) Prior Publication Data
US 2021/0340231 A1    Nov. 4, 2021

(30) Foreign Application Priority Data
Oct. 10, 2018 (CN) .......................... 201811179512.3

(51) Int. Cl.
*C07K 16/18*    (2006.01)
*G01N 33/68*    (2006.01)

(52) U.S. Cl.
CPC ......... *C07K 16/18* (2013.01); *G01N 33/6893* (2013.01); *C07K 2317/565* (2013.01); *C07K 2317/92* (2013.01); *G01N 2800/12* (2013.01); *G01N 2800/324* (2013.01)

(58) Field of Classification Search
CPC .............. C07K 16/18; C07K 2317/565; C07K 2317/92; C07K 2317/24; C07K 2317/31; C07K 2317/55; C07K 2317/569; C07K 2317/622; G01N 2333/4712; G01N 2800/12; G01N 2800/324; G01N 2800/325; G01N 33/6887; G01N 33/6893; G01N 2800/32; G01N 33/6857; C12N 15/85
See application file for complete search history.

(56) References Cited

U.S. PATENT DOCUMENTS

| | | | |
|---|---|---|---|
| 2008/0152649 A1* | 6/2008 | Chamberlain | ..... C07K 16/2863 536/23.53 |
| 2008/0269467 A1* | 10/2008 | Allan | ..................... A61P 35/00 530/387.3 |
| 2014/0206847 A1 | 7/2014 | Endoh | |

FOREIGN PATENT DOCUMENTS

| CN | 1495196 A | 5/2004 |
|---|---|---|
| CN | 101942416 A | 1/2011 |
| CN | 103173420 A | 6/2013 |
| CN | 107557345 A | 1/2018 |
| CN | 107603955 A | 1/2018 |
| JP | 2016141649 A | 8/2016 |
| WO | 2010099079 A1 | 9/2010 |
| WO | 2011068680 A1 | 6/2011 |
| WO | 2013175678 A1 | 11/2013 |

OTHER PUBLICATIONS

Extended European Search Report for European Application No. 19870959.4, mailed Jun. 10, 2022, (8 pages).
Lee, G. and Liu, S. (2015) "Monoclonal Antibodies Against Human Cardiac Troponin I for Immunoassays II," Monoclonal Antibodies in Immunodiagnosis and Immunotherapy, 34:169-173.
Conroy, P. (2011) "Exploiting Novel Antibodies for the Early Detection of Cardiac Disease," PhD thesis, Biomedical Diagnostic Institute (BDI) in the School of Biotechnology, Dublin City University, (350 pages).
Conroy, P.J., et al. (2012) "Cardiac troponin I: a case study in rational antibody design for human diagnostics," Protein Engineering, Design & Selection, 25:295-305.
Korean Office Action for Korean Counterpart Application No. 10-2021-7012109, mailed Jun. 24, 2024, (14 pages).
International Search Report for International Application No. PCT/CN2019/108682, mailed Jan. 3, 2020, (6 pages).
Written Decision on Registration for Korean Counterpart Application No. 10-2021-7012109, mailed Jan. 21, 2025, 9 pages.

* cited by examiner

*Primary Examiner* — Galina M. Yakovleva
(74) *Attorney, Agent, or Firm* — Kagan Binder, PLLC

(57) ABSTRACT

The present invention provides an isolated binding protein comprising a cTnI antigen binding domain. The antigen binding domain comprises at least one complementarity determining region selected from amino acid sequences defined herein, or has sequence identity of at least 80% to the complementarity determining region of said amino acid sequence and an affinity of $K_D \leq 1.41 \times 10^{-9}$ mol/L to cTnI. The binding protein can be used for detection of cTnI protein.

20 Claims, 1 Drawing Sheet
Specification includes a Sequence Listing.

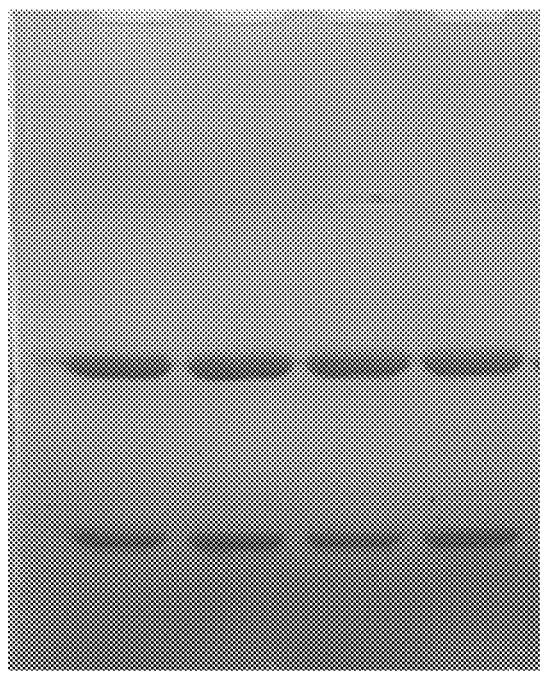

RECOMBINANT ANTIBODY AGAINST HUMAN CARDIAC TROPONIN I

CROSS REFERENCE TO RELATED APPLICATIONS

This application claims priority to International Application No. PCT/CN2019/108682, filed Sep. 27, 2019, which claims priority to Chinese Patent Application No. 201811179512.3, filed on Oct. 10, 2018, and entitled "Recombinant Antibody Against Human Cardiac Troponin I", wherein the contents of said applications are hereby incorporated by reference in their entireties. Also, the entire contents of the ASCII text file entitled "ACL0099US_Sequence_Listing_V2.txt" created on Jun. 27, 2024, having a size of 16,553 bytes is incorporated herein by reference.

REFERENCE TO SEQUENCE LISTING

This application contains a Sequence Listing in a computer readable form, submitted via USPTO Patent Center. The entire contents of the ASCII text file entitled "ACL0099US_Sequence_Listing_V2.txt" created on May 11, 2024, and having a size of 16,542 bytes, is incorporated herein by reference.

TECHNICAL FIELD

The present disclosure relates to the fields of immunological technology, in particular to an anti-human cardiac troponin I recombinant antibody.

BACKGROUND

Before the 1980s, the activity of cardiac enzyme profile has been always regarded by the World Health Organization (WHO) as one of the diagnostic criteria for acute myocardial infarction (AMI). At the end of the 1980s, researchers discovered that troponin (Tn) has higher sensitivity and specificity than biomarkers such as phosphocreatine kinase (CK), phosphocreatine kinase-MB (CK-MB), lactate dehydrogenase, aspartate aminotransferase, and the like. Cardiac troponin I (cTnI), which exists only in the myocardium, is a marker of myocardial cells, and its abnormal changes may affect the diastolic and contraction function of the heart. cTnI can be used for the diagnosis of myocardial necrosis, the determination of myocardial damage and so on, and has become one of the most sensitive and specific markers for cardiomyocyte damage. cTnI is recognized as a major biochemical marker for rapid diagnosis of AMI and acute coronary syndrome (ACS) and for assisting in the risk stratification of ACS and reflecting its prognosis.

Generally, cTnI in the blood of normal people has a content less than 0.3 µg/L. When the integrity of myocardial cell membrane is damaged due to ischemia or hypoxia, free cTnI may quickly penetrate through the cell membrane and enter the bloodstream. Therefore, rapid, sensitive and accurate determination of cTnI and its variation trend in human blood in the early stage of onset has clinical significance for the diagnosis of acute myocardial infarction, the risk stratification of acute coronary syndrome, the monitoring of myocardial damage caused by various factors, etc. Methods used to clinically detect cTnI levels include enzyme-linked immunosorbent assay (ELISA), chemiluminescence, colloidal gold, etc. Various methods have their respective advantages and disadvantages, but all require specific monoclonal antibodies against cTnI.

The existing cTnI antibodies cannot be well applied in the detection of cTnI protein due to their low activity and poor affinity. Therefore, there is a strong demand in the art for antibodies that effectively and specifically bind to and detect cTnI.

SUMMARY

The present disclosure relates to a novel isolated binding protein comprising cardiac troponin I (cTnI) antigen-binding domain, and the preparation and application of the binding protein were studied.

The antigen-binding domain comprises at least one complementarity determining region, which has an amino acid sequence as follows; or which has at least 80% sequence identity to the complementarity determining region having the amino acid sequence as follows and has an affinity for the cardiac troponin I at a $K_D$ value that is less than or equal to $1.41 \times 10^{-9}$ mol/L:

a complementarity determining region CDR-VH1 having a sequence of G-F-N-X1-K-X2-Y-X3-M-H (SEQ ID NO. 23), where
X1 is L or I, X2 is D or E, and X3 is F or Y;
a complementarity determining region CDR-VH2 having a sequence of R-I-X1-P-E-D-X2-E-T-X3-Y-A-P-E (SEQ ID NO. 24), where
X1 is E or D, X2 is A or G, and X3 is R or K;
a complementarity determining region CDR-VH3 having a sequence of Y-Y-X1-S-Y-X2-P-F-V-Y (SEQ ID NO. 25), where
X1 is T or S, and X2 is I, L or V;
a complementarity determining region CDR-VL1 having a sequence of Q-S-X1-X2-Y-S-N-X3-H-T-Y (SEQ ID NO. 26), where
X1 is I or L, X2 is I or L, and X3 is R or K;
a complementarity determining region CDR-VL2 having a sequence of Q-X1-S-X2-R-F-S (SEQ ID NO. 27), where
X1 is I, L or V, and X2 is N or Q;
a complementarity determining region CDR-VL3 having a sequence of S-X1-S-T-H-X2-P-X3-T (SEQ ID NO. 28), where
X1 is Q or N, X2 is L or I, and X3 is F or Y.

An important advantage is that the binding protein has strong activity and high affinity for human cTnI protein.

In one or more embodiments,
in the complementarity determining region CDR-VH1, X2 is D;
in the complementarity determining region CDR-VH2, X1 is D;
in the complementarity determining region CDR-VH3, X1 is S;
in the complementarity determining region CDR-VL1, X3 is R;
in the complementarity determining region CDR-VL2, X2 is N.
in the complementarity determining region CDR-VL3, X1 is Q;

In one or more embodiments, in the complementarity determining region CDR-VH1, X1 is L.

In one or more embodiments, in the complementarity determining region CDR-VH1, X1 is I.

In one or more embodiments, in the complementarity determining region CDR-VH1, X3 is F.

In one or more embodiments, in the complementarity determining region CDR-VH1, X3 is Y.

In one or more embodiments, in the complementarity determining region CDR-VH2, X2 is A.

In one or more embodiments, in the complementarity determining region CDR-VH2, X2 is G.

In one or more embodiments, in the complementarity determining region CDR-VH2, X3 is R.

In one or more embodiments, in the complementarity determining region CDR-VH2, X3 is K.

In one or more embodiments, in the complementarity determining region CDR-VH3, X2 is I.

In one or more embodiments, in the complementarity determining region CDR-VH3, X2 is L.

In one or more embodiments, in the complementarity determining region CDR-VH3, X2 is V.

In one or more embodiments, in the complementarity determining region CDR-VL1, X1 is I.

In one or more embodiments, in the complementarity determining region CDR-VL1, X1 is L.

In one or more embodiments, in the complementarity determining region CDR-VL1, X2 is I.

In one or more embodiments, in the complementarity determining region CDR-VL1, X2 is L.

In one or more embodiments, in the complementarity determining region CDR-VL2, X1 is I.

In one or more embodiments, in the complementarity determining region CDR-VL2, X1 is L.

In one or more embodiments, in the complementarity determining region CDR-VL2, X1 is V.

In one or more embodiments, in the complementarity determining region CDR-VL3, X2 is L.

In one or more embodiments, in the complementarity determining region CDR-VL3, X2 is I.

In one or more embodiments, in the complementarity determining region CDR-VL3, X3 is F.

In one or more embodiments, in the complementarity determining region CDR-VL3, X3 is Y.

In one or more embodiments, the mutation site of each of the complementarity determining regions is any one selected from the following mutation combinations:

| Site | CDR-VH1 X1/X3 | CDR-VH2 X2/X3 | CDR-VH3 X2 | CDR-VL1 X1/X2 | CDR-VL2 X1 | CDR-VL3 X2/X3 |
|---|---|---|---|---|---|---|
| Mutation combination 1 | L/F | A/R | I | I/I | I | L/F |
| Mutation combination 2 | L/Y | A/K | L | I/L | L | L/Y |
| Mutation combination 3 | I/F | G/R | V | L/I | V | I/F |
| Mutation combination 4 | I/Y | G/K | L | L/L | L | I/Y |
| Mutation combination 5 | L/F | A/K | V | L/L | V | L/F |
| Mutation combination 6 | L/Y | G/R | I | I/I | I | I/F |
| Mutation combination 7 | I/F | G/K | V | I/L | V | I/Y |
| Mutation combination 8 | I/Y | A/R | I | L/I | I | L/Y |
| Mutation combination 9 | L/F | G/R | L | L/I | L | L/F |
| Mutation combination 10 | L/Y | G/K | I | L/L | I | I/Y |
| Mutation combination 11 | I/F | A/R | L | I/I | L | L/Y |
| Mutation combination 12 | I/Y | A/K | V | I/L | V | I/F |
| Mutation combination 13 | L/F | G/K | L | I/L | L | L/Y |
| Mutation combination 14 | L/Y | A/R | V | L/I | V | L/F |
| Mutation combination 15 | I/F | A/K | I | L/L | I | I/F |
| Mutation combination 16 | I/Y | G/R | V | I/I | V | I/Y |
| Mutation combination 17 | L/F | A/R | I | L/L | I | L/Y |
| Mutation combination 18 | L/Y | A/R | L | I/I | L | I/Y |
| Mutation combination 19 | I/F | A/K | I | I/L | I | L/F |
| Mutation combination 20 | I/Y | G/R | L | L/I | L | I/F |
| Mutation combination 21 | L/F | G/K | V | L/I | V | I/F |
| Mutation combination 22 | L/Y | A/K | L | L/L | L | L/F |
| Mutation combination 23 | I/F | G/R | V | I/I | V | L/Y |
| Mutation combination 24 | I/Y | G/K | I | I/L | I | I/Y |
| Mutation combination 25 | L/F | A/R | V | L/L | V | I/F |
| Mutation combination 26 | L/Y | G/R | I | I/I | I | L/Y |
| Mutation combination 27 | I/F | G/K | L | I/L | L | L/F |
| Mutation combination 28 | I/Y | A/R | I | L/I | I | I/Y |
| Mutation combination 29 | L/F | A/K | L | L/I | L | L/F |
| Mutation combination 30 | L/Y | G/K | V | L/L | V | L/Y |
| Mutation combination 31 | I/F | A/R | L | I/I | L | I/F |
| Mutation combination 32 | I/Y | A/K | V | I/L | V | I/Y |
| Mutation combination 33 | L/F | G/R | I | I/L | I | L/F |
| Mutation combination 34 | L/Y | A/K | V | L/I | V | I/F |
| Mutation combination 35 | I/F | G/K | I | L/L | I | I/Y |
| Mutation combination 36 | I/Y | A/R | L | I/I | L | L/Y |
| Mutation combination 37 | L/Y | G/R | L | I/I | L | I/Y |
| Mutation combination 38 | I/F | G/K | V | I/L | V | L/Y |
| Mutation combination 39 | I/Y | A/K | I | L/I | I | I/F |
| Mutation combination 40 | L/F | G/R | V | L/I | V | L/Y |
| Mutation combination 41 | L/Y | G/K | I | L/L | I | L/F |
| Mutation combination 42 | I/Y | G/R | I | I/L | I | I/Y |
| Mutation combination 43 | L/F | G/K | L | L/L | L | L/Y |
| Mutation combination 44 | L/Y | A/R | V | I/I | V | I/Y |
| Mutation combination 45 | I/F | A/K | L | I/L | L | L/F |
| Mutation combination 46 | I/Y | G/K | V | L/I | V | I/F |
| Mutation combination 47 | L/F | A/R | I | L/I | I | I/F |
| Mutation combination 48 | L/Y | A/K | V | L/L | V | L/F |
| Mutation combination 49 | I/F | G/R | I | I/I | I | L/Y |

-continued

| Site | CDR-VH1 X1/X3 | CDR-VH2 X2/X3 | CDR-VH3 X2 | CDR-VL1 X1/X2 | CDR-VL2 X1 | CDR-VL3 X2/X3 |
|---|---|---|---|---|---|---|
| Mutation combination 50 | I/Y | A/R | L | I/L | L | I/Y |
| Mutation combination 51 | L/F | A/K | I | I/L | I | I/F |
| Mutation combination 52 | L/Y | G/R | L | L/I | L | L/Y |
| Mutation combination 53 | I/F | A/R | V | L/L | V | L/F |
| Mutation combination 54 | I/Y | A/K | L | I/I | L | I/Y. |

In one or more embodiments, the binding protein includes at least 3 CDRs; or the binding protein includes at least 6 CDRs.

In one or more embodiments, the binding protein is an intact antibody comprising a variable region and a constant region.

In one or more embodiments, the binding protein is a "functional fragment" of an antibody, such as one of nanobody, F(ab')$_2$, Fab', Fab, Fv, scFv, bispecific antibody, and antibody minimal recognition unit.

In one or more embodiments, the binding protein comprises light chain framework regions FR-L1, FR-L2, FR-L3 and FR-L4 having sequences as set forth in SEQ ID NO: 1 to 4, respectively, and/or heavy chain framework regions FR-H1, FR-H2, FR-H3 and FR-H4 having sequences as set forth in SEQ ID NO: 5 to 8, respectively.

In one or more embodiments, the binding protein further comprises an constant region sequence of an antibody.

In one or more embodiments, the constant region sequence is a sequence of a constant region of any one selected from the group consisting of IgG1, IgG2, IgG3, IgG4, IgA, IgM, IgE, and IgD.

In one or more embodiments, the constant region is derived from the following species: cattle, horse, dairy cow, pig, sheep, goat, rat, mouse, dog, cat, rabbit, camel, donkey, deer, mink, chicken, duck, goose, turkey, gamecock, or human.

In one or more embodiments, the constant region is derived from murine.

The constant region sequence of a light chain is as set forth in SEQ ID NO: 9.

The constant region sequence of a heavy chain is as set forth in SEQ ID NO: 10.

According to one aspect of the present disclosure, the present disclosure also relates to an isolated nucleic acid molecule. The nucleic acid molecule is DNA or RNA encoding the binding protein as described above.

According to one aspect of the present disclosure, the present disclosure also relates to a vector comprising the nucleic acid molecule as described above.

According to an aspect of the present disclosure, the present disclosure also relates to a host cell transformed with the vector as described above.

According to an aspect of the present disclosure, the present disclosure also relates to a method for producing the binding protein as described above, the method comprising the following steps:

culturing the host cell as described above in a culture medium under appropriate culture conditions, and recovering binding proteins thus produced from the culture medium or from the cultured host cell.

According to an aspect of the present disclosure, the present disclosure also relates to use of the binding protein as described above in preparation of a diagnostic agent or kit for diagnosing acute myocardial infarction, acute coronary syndrome, pulmonary infarction, unstable angina pectoris, and myocardial damage.

According to an aspect of the present disclosure, the present disclosure also relates to a method for detecting troponin I antigen in a test sample, comprising:
a) contacting the troponin I in the test sample with the binding protein as described above under a condition sufficient for the occurrence of antibody/antigen binding reaction to form an immune complex; and
b) detecting the presence of the immune complex, the presence of the complex indicating the presence of the troponin I antigen in the test sample.

In one or more embodiments, in step a), the immune complex further comprises a second antibody that binds to the binding protein.

In one or more embodiments, in step a), the immune complex further comprises a second antibody that binds to the troponin I antigen.

In one or more embodiments, the enzymes include any one of horseradish peroxidase, alkaline phosphatase and glucose oxidase.

According to an aspect of the present disclosure, the present disclosure also relates to a kit comprising the binding protein as described above.

In one or more embodiments, the troponin I antigen is a cardiac troponin I antigen.

The present disclosure also relates to use of the binding protein described herein in diagnosis of a disease related to cardiac troponin I.

The present disclosure also relates to a method for diagnosing a disease related to cardiac troponin I, comprising:
A) contacting a sample from a subject with the binding protein in the present disclosure for a binding reaction under a condition sufficient for the occurrence of the binding reaction, and
B) detecting an immune complex produced by the binding reaction, wherein the presence of the immune complex indicates the presence of the disease related to cardiac troponin I.

In one or more embodiments, the method is based on fluorescence immunoassay, chemiluminescence immunoassay, colloidal gold immunoassay, radioimmunoassay and/or enzyme-linked immunoassay.

In one or more embodiments, the sample is at least one selected from whole blood, peripheral blood, serum, plasma or myocardial tissue.

In one or more embodiments, the subject is a mammal, such as a primate, for example, human.

In one or more embodiments, the disease related to cardiac troponin I is cardiovascular disease.

In one or more embodiments, the disease related to cardiac troponin I is selected from the group consisting of acute myocardial infarction, acute coronary syndrome, pulmonary infarction, unstable angina, myocardial damage, or a combination thereof.

BRIEF DESCRIPTION OF THE DRAWINGS

In order to more clearly describe the technical solutions in the specific embodiments of the present disclosure or in the prior art, brief description will be made below to the drawings that used in the specific embodiments or the prior art. Obviously, the drawings as described below are some embodiments of the present disclosure. For those of ordinary skill in the art, other drawings can be derived from these drawings without creative work.

FIG. 1 is an electrophoresis image of an anti-human cardiac troponin I recombinant antibody according to the present disclosure.

DETAILED DESCRIPTION OF THE EMBODIMENTS

The present disclosure can be more easily understood through the following description of some embodiments of the present disclosure and the detailed content of the examples included therein.

Before further describing the present disclosure, it should be understood that the present disclosure is not limited to the specific embodiments, since these embodiments are necessarily diverse. It should also be understood that the terms used in this specification are only to illustrate specific embodiments, rather than for limitations, because the scope of the present disclosure will only be defined in the appended claims.

Term Definition

An "isolated binding protein comprising an antigen-binding domain" refers to all proteins/protein fragments containing CDR regions. The term "antibody" includes polyclonal antibodies, monoclonal antibodies, and antigen-compound-binding fragments of these antibodies, including Fab, F(ab')$_2$, Fd, Fv, scFv, bispecific antibody, and antibody minimal recognition unit, as well as single chain derivatives of these antibodies and fragments. The type of the antibody can be selected from the group consisting of IgG1, IgG2, IgG3, IgG4, IgA, IgM, IgE, and IgD. Moreover, the term "antibody" includes naturally-occurring antibodies, as well as non-naturally-occurring antibodies including, for example, chimeric, bifunctional and humanized antibodies, and relevant synthetic isoforms. The term "antibody" can be used interchangeably with "immunoglobulin".

A "variable region" or "variable domain" of an antibody refers to the amino terminal domain of a heavy or light chain of the antibody. The variable domain of the heavy chain may be referred to as "VH". The variable domain of the light chain may be referred to as "VL". These domains are usually the most variable parts of antibodies and contain an antigen-binding site. The variable region of light or heavy chain (VL or VH) is composed of three hypervariable regions termed "complementarity determining regions" or "CDRs", and framework regions that separates the three CDRs. The extents of the framework region and CDRs have been precisely defined, for example in Kabat (see, E. Kabat, et al. Sequences of Proteins of Immunological Interest, U.S. Department of Health and Human Services (1983)), and Chothial. The framework regions of the antibody, that is, the framework region that constitutes the combination of the light chain and the heavy chain, functions to locate the CDRs and bring the CDRs into alignment, and the CDRs are mainly responsible for binding to the antigen.

As used herein, "framework region" or "FR" means those regions within the variable domain of an antibody except those defined to be CDR. Each antibody variable domain framework region can be further subdivided into adjacent regions (FR1, FR2, FR3, and FR4) separated by CDRs.

Normally, the variable regions VL/VH of the heavy chain and light chain can be obtained by arranging and linking the following numbered CDRs and FRs in the following combination: FR1-CDR1-FR2-CDR2-FR3-CDR3-FR4.

As used herein, the terms "purified" or "isolated" in connection with a polypeptide or nucleic acid means that the polypeptide or nucleic acid is not in its natural medium or in its natural form. Thus, the term "isolated" includes a polypeptide or nucleic acid extracted from its original environment, for example, from the natural environment if it is naturally occurring. For example, an isolated polypeptide generally does not comprise at least some proteins or other cellular components to which the polypeptide usually binds, or that are normally mixed with the polypeptide, or that are in the solution. The isolated polypeptide includes the naturally-produced polypeptide contained in a cell lysate, the polypeptide in purified or partially purified form, the recombinant polypeptide, the polypeptide expressed or secreted by cells, and the polypeptide in heterologous host cells or cultures. The term isolated or purified in connection with nucleic acid indicates that the nucleic acid is, for example, not in its natural genomic background, e.g., in a vector, as an expression cassette, linked to a promoter, or artificially introduced into a heterologous host cell.

As used herein, the term "bispecific antibody" or "bifunctional antibody" refers to an artificial hybrid binding protein with two different pairs of heavy/light chains and two different binding sites. Bispecific binding proteins can be produced by a variety of methods, including hybridoma fusion or Fab' fragments linking.

As used herein, the term "sequence identity" refers to the similarity between at least two different sequences. This percent identity can be determined by standard algorithms, for example, the Basic Local Alignment Search Tool (BLAST); the algorithm established by Needleman et al.; or the algorithm established by Meyers et al. In one or more embodiments, a set of parameters may be the Blosum 62 scoring matrix with a gap penalty of 12, a gap extend penalty of 4, and a frameshift gap penalty of 5. In one or more embodiments, the percent identity between two amino acid or nucleotide sequences can also be determined using the algorithm as described in Meyers and Miller ((1989) CABIOS 4: 11-17), which has been incorporated into the ALIGN program (version 2.0), using a PAM120 weight residue table, a gap length penalty of 12, and a gap penalty of 4. The percent identity is usually calculated by comparing sequences of similar length.

As used herein, the term "affinity" refers to the binding strength of the antigen-binding domain of a binding protein or antibody to an antigen or an epitope of an antigen. Affinity can be measured by KD value. A smaller KD value means a greater affinity.

Exemplary Embodiments of the Present Disclosure

The present disclosure provides an isolated binding protein comprising an antigen-binding domain, wherein the antigen-binding domain comprises at least one complementarity determining region, which has an amino acid sequence as follows; or which has at least 80% sequence identity to the complementarity determining region having the amino acid sequence as follows and has an affinity for the cardiac troponin I at a $K_D$ value that is less than or equal to $1.41 \times 10^{-9}$ mol/L:

a complementarity determining region CDR-VH1 having a sequence of G-F-N-X1-K-X2-Y-X3-M-H (SEQ ID NO. 23), where X1 is L or I, X2 is D or E, and X3 is F or Y;

a complementarity determining region CDR-VH2 having a sequence of R-I-X1-P-E-D-X2-E-T-X3-Y-A-P-E (SEQ ID NO. 24), where
X1 is E or D, X2 is A or G, and X3 is R or K;
a complementarity determining region CDR-VH3 having a sequence of Y-Y-X1-S-Y-X2-P-F-V-Y (SEQ ID NO. 25), where
X1 is T or S, and X2 is I, L or V;
a complementarity determining region CDR-VL1 having a sequence of Q-S-X1-X2-Y-S-N-X3-H-T-Y (SEQ ID NO. 26), where
X1 is I or L, X2 is I or L, and X3 is R or K;
a complementarity determining region CDR-VL2 having a sequence of Q-X1-S-X2-R-F-S (SEQ ID NO. 27), where
X1 is I, L or V, and X2 is N or Q;
a complementarity determining region CDR-VL3 having a sequence of S-X1-S-T-H-X2-P-X3-T (SEQ ID NO. 28), where
X1 is Q or N, X2 is L or I, and X3 is F or Y.

In one or more embodiments, the antigen-binding domain has at least 50%, or at least 55%, or at least 60%, or at least 65%, or at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% sequence identity to the complementarity determining region having the amino acid sequence as follows and has an affinity for the cardiac troponin I at a $K_D$ value that is less than or equal to $1.41 \times 10^{-9}$ mol/L, for example, $1 \times 10^{-10}$ mol/L, $2 \times 10^{-10}$ mol/L, $3 \times 10^{-10}$ mol/L, $4 \times 10^{-10}$ mol/L, $4.5 \times 10^{-10}$ mol/L, $5 \times 10^{-10}$ mol/L, $6 \times 10^{-10}$ mol/L, $7 \times 10^{-10}$ mol/L, $8 \times 10^{-10}$ mol/L, $9 \times 10^{-10}$ mol/L, $1 \times 10^{-11}$ mol/L, $3 \times 10^{-11}$ mol/L, $5 \times 10^{-11}$ mol/L, $5 \times 10^{-11}$ mol/L, $7 \times 10^{-11}$ mol/L, $9 \times 10^{-11}$ mol/L or $1 \times 10^{-9}$ mol/L, or at a $K_D$ value that is greater than or equal to $1.68 \times 10^{-10}$ mol/L and less than or equal to $1.41 \times 10^{-9}$ mol/L, or at a $K_D$ value that is less than or equal to $1 \times 10^{-10}$ mol/L, $2 \times 10^{-10}$ mol/L, $3 \times 10^{-10}$ mol/L, $4 \times 10^{-10}$ mol/L, $4.5 \times 10^{-10}$ mol/L, $5 \times 10^{-10}$ mol/L, $6 \times 10^{-10}$ mol/L, $7 \times 10^{-10}$ mol/L, $8 \times 10^{-10}$ mol/L, $9 \times 10^{-10}$ mol/L, $1 \times 10^{-11}$ mol/L, $3 \times 10^{-11}$ mol/L, $5 \times 10^{-11}$ mol/L, $5 \times 10^{-11}$ mol/L, $7 \times 10^{-11}$ mol/L, or $9 \times 10^{-11}$ mol/L.

The affinity is measured according to the method in the present disclosure.

In one or more embodiments,
in the complementarity determining region CDR-VH1, X2 is D;
in the complementarity determining region CDR-VH2, X1 is D;
in the complementarity determining region CDR-VH3, X1 is S;
in the complementarity determining region CDR-VL1, X3 is R;
in the complementarity determining region CDR-VL2, X2 is N.
in the complementarity determining region CDR-VL3, X1 is Q;

In one or more embodiments, in the complementarity determining region CDR-VH1, X1 is L.
In one or more embodiments, in the complementarity determining region CDR-VH1, X1 is I.
In one or more embodiments, in the complementarity determining region CDR-VH1, X3 is F.
In one or more embodiments, in the complementarity determining region CDR-VH1, X3 is Y.
In one or more embodiments, in the complementarity determining region CDR-VH2, X2 is A.
In one or more embodiments, in the complementarity determining region CDR-VH2, X2 is G.
In one or more embodiments, in the complementarity determining region CDR-VH2, X3 is R.
In one or more embodiments, in the complementarity determining region CDR-VH2, X3 is K.
In one or more embodiments, in the complementarity determining region CDR-VH3, X2 is I.
In one or more embodiments, in the complementarity determining region CDR-VH3, X2 is L.
In one or more embodiments, in the complementarity determining region CDR-VH3, X2 is V.
In one or more embodiments, in the complementarity determining region CDR-VL1, X1 is I.
In one or more embodiments, in the complementarity determining region CDR-VL1, X1 is L.
In one or more embodiments, in the complementarity determining region CDR-VL1, X2 is I.
In one or more embodiments, in the complementarity determining region CDR-VL1, X2 is L.
In one or more embodiments, in the complementarity determining region CDR-VL2, X1 is I.
In one or more embodiments, in the complementarity determining region CDR-VL2, X1 is L.
In one or more embodiments, in the complementarity determining region CDR-VL2, X1 is V.
In one or more embodiments, in the complementarity determining region CDR-VL3, X2 is L.
In one or more embodiments, in the complementarity determining region CDR-VL3, X2 is I.
In one or more embodiments, in the complementarity determining region CDR-VL3, X3 is F.
In one or more embodiments, in the complementarity determining region CDR-VL3, X3 is Y.

In one or more embodiments, the mutation site of each of the complementarity determining regions is selected from any one of the following mutation combinations:

| Site | CDR-VH1 X1/X3 | CDR-VH2 X2/X3 | CDR-VH3 X2 | CDR-VL1 X1/X2 | CDR-VL2 X1 | CDR-VL3 X2/X3 |
|---|---|---|---|---|---|---|
| Mutation combination 1 | L/F | A/R | I | I/I | I | L/F |
| Mutation combination 2 | L/Y | A/K | L | I/L | L | L/Y |
| Mutation combination 3 | I/F | G/R | V | L/I | V | I/F |
| Mutation combination 4 | I/Y | G/K | L | L/L | L | I/Y |
| Mutation combination 5 | L/F | A/K | V | L/L | V | L/F |
| Mutation combination 6 | L/Y | G/R | I | I/I | I | I/F |
| Mutation combination 7 | I/F | G/K | V | I/L | V | I/Y |
| Mutation combination 8 | I/Y | A/R | I | L/I | I | L/Y |
| Mutation combination 9 | L/F | G/R | L | L/I | L | L/F |
| Mutation combination 10 | L/Y | G/K | I | L/L | I | I/Y |
| Mutation combination 11 | I/F | A/R | L | I/I | L | L/Y |
| Mutation combination 12 | I/Y | A/K | V | I/L | V | I/F |
| Mutation combination 13 | L/F | G/K | L | I/L | L | L/Y |

| Site | CDR-VH1 X1/X3 | CDR-VH2 X2/X3 | CDR-VH3 X2 | CDR-VL1 X1/X2 | CDR-VL2 X1 | CDR-VL3 X2/X3 |
|---|---|---|---|---|---|---|
| Mutation combination 14 | L/Y | A/R | V | L/I | V | L/F |
| Mutation combination 15 | I/F | A/K | I | L/L | I | I/F |
| Mutation combination 16 | I/Y | G/R | V | I/I | V | I/Y |
| Mutation combination 17 | L/F | A/R | I | L/L | I | L/Y |
| Mutation combination 18 | L/Y | A/R | L | I/I | L | I/Y |
| Mutation combination 19 | I/F | A/K | I | I/L | I | L/F |
| Mutation combination 20 | I/Y | G/R | L | L/I | L | I/F |
| Mutation combination 21 | L/F | G/K | V | L/I | V | I/F |
| Mutation combination 22 | L/Y | A/K | L | L/L | L | L/F |
| Mutation combination 23 | I/F | G/R | V | I/I | V | L/Y |
| Mutation combination 24 | I/Y | G/K | I | I/L | I | I/Y |
| Mutation combination 25 | L/F | A/R | V | L/L | V | I/F |
| Mutation combination 26 | L/Y | G/R | I | I/I | I | L/Y |
| Mutation combination 27 | I/F | G/K | L | I/L | L | L/F |
| Mutation combination 28 | I/Y | A/R | I | L/I | I | I/Y |
| Mutation combination 29 | L/F | A/K | L | L/I | L | L/F |
| Mutation combination 30 | L/Y | G/K | V | L/L | V | L/Y |
| Mutation combination 31 | I/F | A/R | L | I/I | L | I/F |
| Mutation combination 32 | I/Y | A/K | V | I/L | V | I/Y |
| Mutation combination 33 | L/F | G/R | I | I/I | I | L/F |
| Mutation combination 34 | L/Y | A/K | V | L/I | V | I/F |
| Mutation combination 35 | I/F | G/K | I | I/L | I | I/Y |
| Mutation combination 36 | I/Y | A/R | L | I/I | L | L/Y |
| Mutation combination 37 | L/Y | G/R | L | I/I | L | I/Y |
| Mutation combination 38 | I/F | G/K | V | I/L | V | L/Y |
| Mutation combination 39 | I/Y | A/K | I | L/I | I | I/F |
| Mutation combination 40 | L/F | G/R | V | L/I | V | L/Y |
| Mutation combination 41 | L/Y | G/K | I | L/L | I | L/F |
| Mutation combination 42 | I/Y | G/R | I | I/L | I | I/Y |
| Mutation combination 43 | L/F | G/K | L | L/L | L | L/Y |
| Mutation combination 44 | L/Y | A/R | V | I/I | V | I/Y |
| Mutation combination 45 | I/F | A/K | I | I/L | I | L/F |
| Mutation combination 46 | I/Y | G/K | V | L/I | V | I/F |
| Mutation combination 47 | L/F | A/R | I | L/I | I | I/F |
| Mutation combination 48 | L/Y | A/K | V | L/L | V | L/F |
| Mutation combination 49 | I/F | G/R | I | I/I | I | L/Y |
| Mutation combination 50 | I/Y | A/R | L | I/L | L | I/Y |
| Mutation combination 51 | L/F | A/K | I | I/L | I | I/F |
| Mutation combination 52 | L/Y | G/R | L | L/I | L | L/Y |
| Mutation combination 53 | I/F | A/R | V | L/L | V | L/F |
| Mutation combination 54 | I/Y | A/K | L | I/I | L | I/Y |

In one or more embodiments, X1 appearing in the six CDR regions of the binding protein described in the present disclosure each independently represents an amino acid defined in the present disclosure; X2 appearing in the six CDR regions of the binding protein described in the present disclosure each independently represents an amino acid defined in the present disclosure; and X3 appearing in the six CDR regions of the binding protein described in the present disclosure each independently represents an amino acid defined in the present disclosure.

In one or more embodiments, the binding protein includes at least 3 CDRs; or the binding protein includes at least 6 CDRs.

In one or more embodiments, the binding protein is an intact antibody comprising a variable region and a constant region.

In one or more embodiments, the binding protein is a "functional fragment" of an antibody, such as one of nanobody, $F(ab')_2$, Fab', Fab, Fv, scFv, bispecific antibody, and antibody minimal recognition unit.

scFv (sc=single chain), bispecific antibodies (diabodies).

The "functional fragment" described in the present disclosure specifically refers to an antibody fragment having the same specificity for cTnI as the parent antibody. In addition to the above functional fragments, any fragments having an increased half-life are also included.

Generally, these functional fragments have the same binding specificity as the antibody from which they are derived. From the content recited in the present disclosure, those skilled in the art infer that the functional fragments as described above can be obtained using the antibody fragments of the present disclosure through methods such as enzymatic digestion (including pepsin or papain) and/or through chemical reduction methods to split disulfide bonds.

Antibody fragments can also be obtained by recombinant genetic techniques that are also known to those skilled in the art or by peptide synthesis, for example, through automatic peptide synthesizers, such as those sold by Applied BioSystems.

In one or more embodiments, the binding protein comprises light chain framework regions FR-L1, FR-L2, FR-L3 and FR-L4 having sequences as set forth in SEQ ID NO: 1 to 4, respectively, and/or heavy chain framework regions FR-H1, FR-H2, FR-H3 and FR-H4 having sequences as set forth in SEQ ID NO: 5 to 8, respectively.

It should be noted that, in order to form a humanized antibody, the framework region may be derived from human, in addition to the amino acid sequence disclosed above in the present disclosure.

In one or more embodiments, the binding protein further comprises an constant region sequence of an antibody.

In one or more embodiments, the constant region sequence is a sequence of a constant region of any one selected from the group consisting of IgG1, IgG2, IgG3, IgG4, IgA, IgM, IgE, and IgD.

In one or more embodiments, the constant region is derived from the following species: cattle, horse, dairy cow, pig, sheep, goat, rat, mouse, dog, cat, rabbit, camel, donkey, deer, mink, chicken, duck, goose, turkey, gamecock, or human.

In one or more embodiments, the constant region is derived from murine.

The constant region sequence of a light chain is as set forth in SEQ ID NO: 9.

The constant region sequence of a heavy chain is as set forth in SEQ ID NO: 10.

According to one aspect of the present disclosure, the present disclosure also relates to an isolated nucleic acid molecule. The nucleic acid molecule is DNA or RNA encoding the binding protein as described above.

According to one aspect of the present disclosure, the present disclosure also relates to a vector comprising the nucleic acid molecule as described above.

The present disclosure further includes at least one nucleic acid construct encoding the nucleic acid molecule as described above, such as a plasmid, and further an expression plasmid. A method for constructing the vector will be described in an embodiment of the present application.

According to an aspect of the present disclosure, the present disclosure also relates to a host cell transformed with the vector as described above.

The host cell may be a eukaryotic cell, such as a mammalian cell.

In one or more embodiments, the host cell is a CHO cell.

According to an aspect of the present disclosure, the present disclosure also relates to a method for producing the binding protein as described above, the method comprising the following steps:

culturing the host cell as described above in a culture medium under appropriate culture conditions, and recovering binding proteins thus produced from the culture medium or from the cultured host cell.

According to an aspect of the present disclosure, the present disclosure also relates to use of the binding protein as described above in preparation of a diagnostic agent or kit for diagnosing acute myocardial infarction, acute coronary syndrome, pulmonary infarction, unstable angina pectoris, and myocardial damage.

According to an aspect of the present disclosure, the present disclosure also relates to a method for detecting troponin I antigen in a test sample, comprising:
a) contacting the troponin I in the test sample with the binding protein as described above under a condition sufficient for the occurrence of antibody/antigen binding reaction to form an immune complex; and
b) detecting the presence of the immune complex, the presence of the complex indicating the presence of the troponin I antigen in the test sample.

In this embodiment, the binding protein can be labeled with an indicator for showing signal intensity, so that the complex is easily detected.

In one or more embodiments, in step a), the immune complex further comprises a second antibody that binds to the binding protein.

In this embodiment, the binding protein, in a form of a first antibody, forms a paired antibody with the second antibody for binding to different epitopes of the cTnI.

The second antibody can be labeled with an indicator for showing signal intensity, so that the complex is easily detected.

In one or more embodiments, in step a), the immune complex further comprises a second antibody that binds to the troponin I antigen.

In this embodiment, the binding protein serves as the antigen of the second antibody. The second antibody can be labeled with an indicator for showing signal intensity, so that the complex is easily detected.

In one or more embodiments, the indicator for showing signal intensity includes any of fluorescent substance, quantum dot, digoxigenin-labeled probe, biotin, radioisotope, radiocontrast agent, paramagnetic ion fluorescent microsphere, electron-dense material, chemiluminescent markers, ultrasound contrast agents, photosensitizers, colloidal gold or enzymes.

In one or more embodiments, the fluorescent substance includes any of Alexa Fluor™ 350, Alexa Fluor™ 405, Alexa Fluor™ 430, Alexa Fluor™488, Alexa Fluor™ 555, Alexa Fluor™ 647, AMCA, aminoacridine, BODIPY™ 630/650, BODIPY™650/665, BODIPY™-FL Dye, BODIPY™-R6G, BODIPY™-TMR, BODIPY™-TRX, 5-carboxy-4',5'-dichloro-2',7'-dimethoxyfluorescein, 5-carboxy-2',4',5',7'-tetrachlorofluorescein, 5-carboxyfluorescein, 5-carboxyrhodamine, 6-carboxyrhodamine, 6-carboxytetramethylrhodamine, Cascade Blue™ Dye, Cy2®, Cy3®, Cy5®, Cy7@, 6-FAM, dansyl chloride, fluorescein, HEX™ dye, 6-JOE™, NBD (7-nitrobenzo-2-oxa-1,3-diazole), Oregon Green™ 488 Dye, Oregon Green™ 500 Dye, Oregon Green™ 514 Dye, Pacific Blue™ Dye, o-phthalic acid, p-phthalic acid, m-phthalic acid, cresol solid violet, cresol blue violet, brilliant cresol blue, p-aminobenzoic acid, erythrosine, phthalocyanine, azomethine, cyanine, xanthine, succinylfluorescein, rare earth metal cryptate, europium tris-bipyridine diamine, europium cryptate or chelate, diamine, biscyanin, La Jolla blue dye, allophycocyanin, B-allococyanin, C-phycocyanin, R-phycocyanin, thiamine, phycoerythrin, R-phycoerythrin, REG, rhodamine green, rhodamine isothiocyanate, rhodamine red, ROX™, TAMRA™, TET™, TRIT (tetramethylrhodamine isothiol), tetramethylrhodamine and Texas Red™.

In one or more embodiments, the radioisotope includes any of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$mTc, $^{94}$Tc, $^{99}$mTc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb and $^{83}$Sr.

In one or more embodiments, the enzymes include any of horseradish peroxidase, alkaline phosphatase and glucose oxidase.

In one or more embodiments, the fluorescent microsphere is a polystyrene fluorescent microsphere, inside which fluorescent europium, a rare earth ion, is packaged.

According to an aspect of the present disclosure, the present disclosure also relates to a kit comprising the binding protein as described above.

In one or more embodiments, the troponin I antigen is a cardiac troponin I antigen.

The present disclosure also relates to use of the binding protein described herein in diagnosis of a disease related to cardiac troponin I.

As used herein, the term "a disease related to cardiac troponin I" refers to diseases in which cardiac troponin I, including the protein itself or a nucleic acid encoding it, serves as a marker. In particular, in one or more embodiments of the present disclosure, the diseases related to cardiac troponin I may refer to diseases characterized by an increased level of cardiac troponin I in blood. In one or more embodiments of the present disclosure, the disease related to cardiac troponin I may refer to diseases characterized by a decreased level of cardiac troponin I in myocardial tissue and myocardial cells.

The present disclosure also relates to a method for diagnosing a disease related to cardiac troponin I, comprising:

A) contacting a sample from a subject with the binding protein in the present disclosure for a binding reaction under a condition sufficient for the occurrence of the binding reaction, and B) detecting an immune complex produced by the binding reaction, wherein the presence of the immune complex indicates the presence of the disease related to cardiac troponin I.

In one or more embodiments, the method is based on fluorescence immunoassay, chemiluminescence immunoassay, colloidal gold immunoassay, radioimmunoassay and/or enzyme-linked immunoassay.

In one or more embodiments, the sample is at least one selected from whole blood, peripheral blood, serum, plasma or myocardial tissue.

In one or more embodiments, the subject is a mammal, such as a primate, for example, human.

In one or more embodiments, the disease related to cardiac troponin I is cardiovascular disease.

In one or more embodiments, the disease related to cardiac troponin I is selected from the group consisting of acute myocardial infarction, acute coronary syndrome, pulmonary infarction, unstable angina, myocardial damage, or a combination thereof.

The embodiments of the present disclosure will be described in detail below in conjunction with examples, but those skilled in the art will understand that the following examples are only used to illustrate the present disclosure, and should not be considered to limit the scope of the present disclosure. The examples shall be carried out in accordance with conventional conditions or conditions recommended by the manufacturer if specific conditions are not indicated in the examples. The reagents or instruments used without indicating their manufacturer are all conventional commercially available products.

Example 1

This example provides an exemplary method for preparing an anti-recombinant antibody against human cardiac troponin I.

S10. Construction of Expression Plasmids:

In this example, the restriction endonuclease and Prime Star DNA Polymerase were purchased from Takara;

MagExtractor-RNA Extraction kit was purchased from TOYOBO.SMARTER™ RACE cDNA Amplification kit was purchased from Takara.

pMD-18T vector was purchased from Takara.

Plasmid Extraction kit was purchased from Tiangen.

The primer synthesis and gene sequencing were done by Invitrogen.

The cell line that secretes the anti-cTnI 5G8 monoclonal antibody was an existing hybridoma cell line and was revived for use.

S11. Design and Synthesis of Primers.

5'RACE forward primers for amplifying a heavy chain and a light chain

SMARTER II A Oligonucleotide:
(SEQ ID NO: 13)
5'>AAGCAGTGGTATCAACGCAGAGTACXXXXX<3';

(SEQ ID NO: 14)
5'-RACE CDS Primer ( 5'-CDS): 5'>(T)25VN<3'
(N = A, C, G, or T; V = A, G, or C);

Universal Primer A Mix (UPM)
(SEQ ID NO: 15)
5'>CTAATACGACTCACTATAGGGCAAGCAGTGGTATCAACGCAG

AGT<3';

Nested-Universal Primer A (NUP):
(SEQ ID NO: 16)
5'>AAGCAGTGGTATCAACGCAGAGT<3';

(SEQ ID NO: 17)
mIg-kR: 5'> CTAACACTCATTCCTGTTGAAGCTCTTGACAAT <3';

(SEQ ID NO: 18)
mIg-HR: 5'> TCATTTACCAGGAGAGTGGGAGAGGC <3'.

S12. Gene Cloning and Sequencing of Antibody Variable Regions

RNA was extracted from the hybridoma cell line that secretes the anti-cTnI 5G8 monoclonal antibody, and used for the synthesis of a first-strand cDNA by utilizing the SMARTER™ RACE cDNA Amplification kit and the SMARTER II A Oligonucleotide and 5'-CDS primer in the kit. The obtained product, i.e. the first-strand cDNA, was served as a template for PCR amplification. A light chain gene was amplified with the Universal Primer A Mix (UPM), the Nested-Universal Primer A (NUP) and the mIg-kR primer, and a heavy chain gene was amplified with the Universal Primer A Mix (UPM), the Nested-Universal Primer A (NUP) and the mIg-HR primer. A target band in a size of about 0.72 KB was amplified with the primer pair for light chain, while a target band in size of about 1.4 KB was amplified with the primer pair for heavy chain. After purification by agarose gel electrophoresis and recovery, the product was subjected to poly-A tail addition reaction and inserted into the pMD-18T vector prior to transformation into DH5a competent cells. After colonies grew, for each of the heavy chain gene and light chain gene, 4 clones were picked, and then sent to Invitrogen for sequencing.

S13. Sequence Analysis of Variable Region Genes of Anti-cTnI 5G8 Antibody

The gene sequences obtained by the above sequencing were put in the IMGT antibody database and analyzed using VNTI11.5 software, confirming that the genes amplified with the primer pairs for heavy chain and light chain were correct. In the gene fragment amplified with the primer pair for light chain, the VL gene, belonging to the VkII gene family, has a 321 bp sequence with a 57 bp leader peptide sequence upstream; and in the gene fragment amplified with the primer pair for heavy chain, the VL gene, belonging to the VH1 gene family, has a 357 bp sequence with a 57 bp leader peptide sequence upstream.

S14. Construction of Recombinant Antibody Expression Plasmid pcDNA™ 3.4 TOPO® vector is a constructed eukaryotic expression vector for the recombinant antibody, into which multiple cloning sites, such as HindIII, BamHI, EcoRI, and the like, had been introduced, and which was named pcDNA 3.4 A expression vector (hereafter referred to as 3.4 A expression vector for short). According to the sequencing results of the above-mentioned antibody variable region genes in pMD-18T, primers specific to the VL and VH genes of the anti-cTnI 5G8 antibody were designed, with HindIII and EcoRI restriction sites and protective bases at both ends. The primers were as follows:

cTnI-5G8-HF:
(SEQ ID NO: 19)
5'> CCCAAGCTTATGGAATGCAGCTGTGTCATGCTCTTCTTC <3';

cTnI-5G8-HR:
(SEQ ID NO: 20)
5'> CCCGAATTCTCATTTACCAGGAGAGTGGGAGAGGC <3';

cTnI-5G8-LF:
(SEQ ID NO: 21)
5'> CCCAAGCTTATGAAGTTGCCTGTTAGGCTGTTGG <3';

cTnI-5G8-LR:
(SEQ ID NO: 22)
5'> CCCGAATTCCTAACACTCATTCCTGTTGAAGCTCTTGACAA <3';

A light chain gene fragment in size of 0.72 KB and a heavy chain gene fragment in size of 1.4 KB were amplified by PCR amplification. The heavy chain and light chain gene fragments were each double digested by HindIII/EcoRI. The 3.4 vector was also double digested by HindIII/EcoRI. After the digested fragments and the vector were purified and recovered, the heavy chain gene and the light chain gene were respectively linked to the 3.4 A expression vector, obtaining recombinant expression plasmids for the heavy chain and for the light chain respectively.

Example 2

Transient Transfection of Recombinant Antibody Expression Plasmid into CHO Cells and Activity Evaluation of Antibody in the Expressed Supernatant The plasmid was diluted to 400 ng/ml with ultrapure water. CHO cells were adjusted at $1.43 \times 10^7$ cells/mL in a centrifuge tube. After 100 μL of the plasmid was mixed with 700 μL of the cells, the mixture was transferred into an electroporation cuvette for electrotransformation and then transferred to 10 mL CD CHO AGT medium, which was cultured in a shaker at 37° C. (8% $CO_2$, amplitude 150). The medium was sampled every day for testing the cell viability. Once the cell viability was less than 50%, the cell culture was centrifuged, and the antibody (which has a light chain and a heave chain having sequences as set forth in SEQ ID NOs: 11 and 12, respectively) was obtained from the supernatant.

In analysis, the complementarity determining regions of the heavy chain was showed as follows:

a CDR-VH1 having a sequence of G-F-N-L(X1)-K-E(X2)-Y-F(X3)-M-H;

a CDR-VH2 having a sequence of R-I-E(X1)-P-E-D-A(X2)-E-T-R(X3)-Y-A-P-E;

a CDR-VH3 having a sequence of Y-Y-T(X1)-S-Y-I(X2)-P-F-V-Y;

the complementarity determining regions of the light chain was showed as follows:

a CDR-VL1 having a sequence of Q-S-I(X1)-I(X2)-Y-S-N-K(X3)-H-T-Y;

a CDR-VL2 having a sequence of Q-I(X1)-S-Q(X2)-R-F-S;

a CDR-VL2 having a sequence of S-N(X1)-S-T-H-L(X2)-P-F(X3)-T;

where X1, X2, and X3 are all sites to be mutated.

TABLE 1

Mutation sites related to antibody activity

| Site | CDR-VH1 X2 | CDR-VH2 X1 | CDR-VH3 X1 | CDR-VL1 X3 | CDR-VL2 X2 | CDR-VL3 X1 |
|---|---|---|---|---|---|---|
| WT | E | E | T | K | Q | N |
| Mutation 1 | D | D | S | R | N | Q |
| Mutation 2 | E | D | T | R | N | Q |
| Mutation 3 | E | D | T | R | Q | Q |
| Mutation 4 | D | E | S | K | N | N |
| Mutation 5 | D | E | S | K | Q | N |

The inventors mutated the CDR sites in WT as described above to obtain an antibody with better activity.

The cTnI quality control after diluted to 1 μg/ml with the coating solution was used for microplate coating at 100 uL per well and left at 4° C. overnight. The next day, the microplate was washed twice with the wash solution and tapped for drying. The blocking solution (20% BSA+80% PBS) was added at 120 μL per well and left for 1 h at 37° C., and the microplate was tapped for drying. The diluted cTn monoclonal antibody was added at 100 μL per well and left for 30 min at 37° C.; then the microplate was washed 5 times with the wash solution and tapped for drying. The goat anti-mouse IgG-HRP was added at 100 μL per well and left for 30 min at 37° C.; then the microplate was washed 5 times with the wash solution and tapped for drying. Colour-developing solution A was added at 50 μL per well, followed by colour-developing solution B at 50 μL per well; the mixed solution was left for 10 min; and stopping solution was added at 50 μL per well. The OD value was read out at 450 nm (reference at 630 nm) on the microplate reader.

TABLE 2

Antibody activity analysis data

| Sample concentration (ug/ml) | WT | Mutation 1 | Mutation 2 | Mutation 3 | Mutation 4 | Mutation 5 |
|---|---|---|---|---|---|---|
| 1000 | 2.039 | 2.401 | 2.378 | 2.349 | 2.219 | 2.197 |
| 200 | 1.901 | 2.395 | 2.417 | 2.370 | 2.148 | 2.204 |
| 40 | 1.762 | 2.348 | 2.300 | 2.249 | 1.976 | 1.943 |
| 8 | 1.598 | 2.066 | 1.798 | 1.857 | 1.753 | 1.694 |
| 1.6 | 0.534 | 0.973 | 0.724 | 0.831 | 0.689 | 0.721 |
| 0.32 | 0.310 | 0.341 | 0.233 | 0.301 | 0.314 | 0.189 |
| 0 | 0.027 | 0.032 | 0.040 | 0.028 | 0.030 | 0.042 |

The affinity data of the specific antibody sequence was further determined in the above table by the method as follows: using the AMC sensor, the purified antibody was diluted with PBST to 10 μg/ml, and the CTNI quality control recombinant protein (PK2-CTNI-1, 170120, produced by the applicant) was serially diluted with PBST to 400 nmol/ml, 200 nmol/ml, 100 nmol/ml, 50 nmol/ml, 25 nmol/ml, 12.5 nmol/ml, 6.25 nmol/ml, and 0 nmol/ml.

Running process was as follows: equilibrating in buffer 1 (PBST) for 60 s, immobilizing the antibody in the antibody solution for 300 s, incubating in buffer 2 (PBST) for 180 s, binding in the antigen solution for 420 s, dissociating in the buffer 2 for 1200 s, regenerating the sensor with 10 mM GLY solution at pH 1.69 and buffer 3, and outputting the data.

In analysis, Mutation 1 in the above table had the best activity effect, thus Mutation 1 was used as the backbone sequence for screening for mutation sites with better potency (ensuring that the antibody obtained by screening has similar activity to that of mutation 1, i.e. antibody activity ±10%). Some of the results were as follows.

TABLE 3

Mutation sites related to antibody affinity

| Site | CDR-VH1 X1/X3 | CDR-VH2 X2/X3 | CDR-VH3 X2 | CDR-VL1 X1/X2 | CDR-VL2 X1 | CDR-VL3 X2/X3 |
|---|---|---|---|---|---|---|
| Mutation 1 | L/F | A/R | I | I/I | I | L/F |
| Mutation 1-1 | L/Y | A/K | L | I/L | L | L/Y |
| Mutation 1-2 | I/F | G/R | V | L/I | V | I/F |
| Mutation 1-3 | I/Y | G/K | L | L/L | L | I/Y |
| Mutation 1-4 | L/F | A/K | V | L/L | V | L/F |
| Mutation 1-5 | L/Y | G/R | I | I/I | I | I/F |
| Mutation 1-6 | I/F | G/K | V | I/L | V | I/Y |
| Mutation 1-7 | I/Y | A/R | I | L/I | I | L/Y |
| Mutation 1-8 | L/F | G/R | L | L/I | L | L/F |
| Mutation 1-9 | L/Y | G/K | I | L/L | I | I/Y |
| Mutation 1-10 | I/F | A/R | L | I/I | L | L/Y |
| Mutation 1-11 | I/Y | A/K | V | I/L | V | I/F |
| Mutation 1-12 | L/F | G/K | L | I/L | L | L/Y |
| Mutation 1-13 | L/Y | A/R | V | L/I | V | L/F |
| Mutation 1-14 | I/F | A/K | I | L/L | I | I/F |
| Mutation 1-15 | I/Y | G/R | V | I/I | V | I/Y |
| Mutation 1-16 | L/F | A/R | I | L/L | I | L/Y |
| Mutation 1-17 | L/Y | A/R | L | I/I | L | I/Y |
| Mutation 1-18 | I/F | A/K | I | I/L | I | L/F |
| Mutation 1-19 | I/Y | G/R | L | L/I | L | I/F |
| Mutation 1-20 | L/F | G/K | V | L/I | V | I/F |
| Mutation 1-21 | L/Y | A/K | L | L/L | L | L/F |
| Mutation 1-22 | I/F | G/R | V | I/I | V | L/Y |
| Mutation 1-23 | I/Y | G/K | I | I/L | I | I/Y |
| Mutation 1-24 | L/F | A/R | V | L/L | V | I/F |
| Mutation 1-25 | L/Y | G/R | I | I/I | I | L/Y |
| Mutation 1-26 | I/F | G/K | L | I/L | L | L/F |
| Mutation 1-27 | I/Y | A/R | I | L/I | I | I/Y |
| Mutation 1-28 | L/F | A/K | L | L/I | L | L/F |
| Mutation 1-29 | L/Y | G/K | V | L/L | V | L/Y |
| Mutation 1-30 | I/F | A/R | L | I/I | L | I/F |
| Mutation 1-31 | I/Y | A/K | V | I/L | V | I/Y |
| Mutation 1-32 | L/F | G/R | I | I/L | I | L/F |
| Mutation 1-33 | L/Y | A/K | V | L/I | V | I/F |
| Mutation 1-34 | I/F | G/K | I | L/L | I | I/Y |
| Mutation 1-35 | I/Y | A/R | L | I/I | L | L/Y |
| Mutation 1-36 | L/Y | G/R | L | I/I | L | I/Y |
| Mutation 1-37 | I/F | A/K | V | I/L | V | L/Y |
| Mutation 1-38 | I/Y | A/K | I | L/I | I | I/F |
| Mutation 1-39 | L/F | G/R | V | L/I | V | L/Y |
| Mutation 1-40 | L/Y | G/K | I | L/L | I | L/F |
| Mutation 1-41 | I/Y | G/R | I | I/L | I | I/Y |
| Mutation 1-42 | L/F | G/K | L | L/L | L | L/Y |
| Mutation 1-43 | L/Y | A/R | V | I/I | V | I/Y |
| Mutation 1-44 | I/F | A/K | L | I/L | L | L/F |
| Mutation 1-45 | I/Y | G/K | V | L/I | V | I/F |
| Mutation 1-46 | L/F | A/R | I | L/I | I | I/F |
| Mutation 1-47 | L/Y | A/K | V | L/L | V | L/F |
| Mutation 1-48 | I/F | G/R | I | I/I | I | L/Y |
| Mutation 1-49 | I/Y | A/R | L | I/L | L | I/Y |
| Mutation 1-50 | L/F | A/K | I | I/L | I | I/F |
| Mutation 1-51 | L/Y | G/R | L | L/I | L | L/Y |
| Mutation 1-52 | I/F | A/R | V | L/L | V | L/F |
| Mutation 1-53 | I/Y | A/K | L | I/I | L | I/Y |

Affinity Analysis

Using the AMC sensor, the purified antibody was diluted with PBST to 10 µg/ml, and the CTNI quality control recombinant protein (PK2-CTNI-1, 170120, produced by the applicant) was serially diluted with PBST to 400 nmol/ml, 200 nmol/ml, 100 nmol/ml, 50 nmol/ml, 25 nmol/ml, 12.5 nmol/ml, 6.25 nmol/ml, and 0 nmol/ml.

Running process was as follows: equilibrating in buffer 1 (PBST) for 60 s, immobilizing the antibody in the antibody solution for 300 s, incubating in buffer 2 (PBST) for 180 s, binding in the antigen solution for 420 s, dissociating in the buffer 2 for 1200 s, regenerating the sensor with 10 mM GLY solution at pH 1.69 and buffer 3, and outputting the data (KD stands for equilibrium dissociation constant, i.e, the affinity; $k_{on}$ stands for binding rate; and $k_{off}$ stands for dissociation rate).

TABLE 4

Affinity analysis data

| | $K_D$ (M) | $K_{on}$ (1/Ms) | $K_{off}$ (1/S) |
|---|---|---|---|
| Mutation 1 | 7.51E-10 | 2.06E+05 | 1.55E-04 |
| Mutation 1-1 | 8.65E-10 | 3.59E+05 | 3.11E-04 |
| Mutation 1-2 | 6.23E-10 | 4.30E+05 | 2.68E-04 |
| Mutation 1-3 | 6.76E-10 | 1.81E+05 | 1.22E-04 |
| Mutation 1-4 | 9.63E-10 | 2.39E+05 | 2.30E-04 |
| Mutation 1-5 | 6.23E-10 | 1.61E+05 | 1.00E-04 |
| Mutation 1-6 | 7.34E-10 | 3.62E+05 | 2.66E-04 |
| Mutation 1-7 | 8.04E-10 | 6.97E+05 | 5.60E-04 |
| Mutation 1-8 | 3.03E-10 | 8.51E+04 | 2.58E-05 |
| Mutation 1-9 | 8.66E-10 | 1.06E+05 | 9.18E-05 |
| Mutation 1-10 | 9.22E-10 | 4.48E+05 | 4.13E-04 |
| Mutation 1-11 | 6.06E-10 | 7.31E+05 | 4.43E-04 |
| Mutation 1-12 | 8.34E-10 | 3.09E+05 | 2.58E-04 |
| Mutation 1-13 | 8.06E-10 | 3.11E+05 | 2.51E-04 |
| Mutation 1-14 | 4.15E-10 | 6.73E+05 | 2.79E-04 |
| Mutation 1-15 | 9.17E-10 | 2.67E+05 | 2.45E-04 |
| Mutation 1-16 | 6.62E-10 | 1.52E+05 | 1.01E-04 |
| Mutation 1-17 | 7.22E-10 | 7.82E+05 | 5.65E-04 |
| Mutation 1-18 | 6.80E-10 | 4.15E+05 | 2.82E-04 |
| Mutation 1-19 | 4.87E-10 | 3.93E+05 | 1.91E-04 |
| Mutation 1-20 | 9.45E-10 | 1.67E+05 | 1.58E-04 |
| Mutation 1-21 | 6.76E-10 | 7.05E+05 | 4.77E-04 |
| Mutation 1-22 | 7.25E-10 | 2.97E+05 | 2.15E-04 |
| Mutation 1-23 | 9.68E-10 | 6.95E+05 | 6.73E-04 |
| Mutation 1-24 | 4.08E-10 | 6.35E+05 | 2.59E-04 |
| Mutation 1-25 | 9.70E-10 | 6.79E+05 | 6.59E-04 |
| Mutation 1-26 | 6.92E-10 | 3.33E+05 | 2.30E-04 |
| Mutation 1-27 | 8.50E-10 | 9.93E+05 | 8.44E-04 |
| Mutation 1-28 | 1.89E-10 | 5.36E+05 | 1.01E-04 |
| Mutation 1-29 | 6.98E-10 | 1.65E+05 | 1.15E-04 |
| Mutation 1-30 | 6.69E-10 | 5.41E+05 | 3.62E-04 |
| Mutation 1-31 | 7.95E-10 | 3.78E+05 | 3.01E-04 |
| Mutation 1-32 | 5.09E-10 | 1.65E+05 | 8.40E-05 |
| Mutation 1-33 | 9.86E-10 | 8.94E+05 | 8.81E-04 |
| Mutation 1-34 | 1.41E-09 | 4.24E+05 | 5.98E-04 |
| Mutation 1-35 | 5.74E-10 | 4.80E+05 | 2.76E-04 |
| Mutation 1-36 | 8.09E-10 | 5.59E+05 | 4.52E-04 |
| Mutation 1-37 | 6.67E-10 | 4.00E+05 | 2.67E-04 |
| Mutation 1-38 | 2.40E-10 | 4.31E+05 | 1.03E-04 |
| Mutation 1-39 | 7.56E-10 | 6.20E+05 | 4.69E-04 |
| Mutation 1-40 | 8.18E-10 | 2.00E+05 | 1.64E-04 |
| Mutation 1-41 | 7.23E-10 | 5.44E+05 | 3.93E-04 |
| Mutation 1-42 | 3.47E-10 | 5.20E+05 | 1.80E-04 |
| Mutation 1-43 | 6.51E-10 | 1.19E+05 | 7.75E-05 |
| Mutation 1-44 | 8.65E-10 | 5.37E+05 | 4.64E-04 |
| Mutation 1-45 | 1.68E-10 | 1.93E+05 | 3.24E-05 |
| Mutation 1-46 | 7.23E-10 | 3.73E+05 | 2.70E-04 |
| Mutation 1-47 | 8.10E-10 | 6.26E+05 | 5.07E-04 |
| Mutation 1-48 | 9.56E-10 | 6.80E+05 | 6.50E-04 |
| Mutation 1-49 | 5.38E-10 | 5.53E+05 | 2.98E-04 |
| Mutation 1-50 | 3.86E-10 | 1.42E+05 | 5.48E-05 |
| Mutation 1-51 | 7.65E-10 | 9.86E+04 | 7.54E-05 |
| Mutation 1-52 | 9.41E-10 | 2.43E+05 | 2.29E-04 |
| Mutation 1-53 | 7.21E-10 | 3.37E+05 | 2.43E-04 |

It can be seen from Table 4 that the mutation sites listed in Table 3 have little effect on the affinity of the antibody.

In order to verify the above results, the above experiments were repeated with WT as the backbone sequence to verify the affinity of the mutation site. Some of the results are as follows.

TABLE 5

Mutations with WT as the backbone

| Site | CDR-VH1 X1/X3 | CDR-VH2 X2/X3 | CDR-VH3 X2 | CDR-VL1 X1/X2 | CDR-VL2 X1 | CDR-VL3 X2/X3 |
|---|---|---|---|---|---|---|
| WT | L/F | A/R | I | I/I | I | L/F |
| WT 1-3 | I/Y | G/K | L | L/L | L | I/Y |
| WT 1-14 | I/F | A/K | I | L/L | I | I/F |
| WT 1-29 | L/Y | G/K | V | L/L | V | L/Y |
| WT 1-50 | L/Y | G/R | L | L/I | L | L/Y |

TABLE 6

Affinity analysis data

| | $K_D$ (M) | $K_{on}$ (1/Ms) | $K_{off}$ (1/S) |
|---|---|---|---|
| WT | 6.70E−10 | 5.61E+05 | 3.76E−04 |
| WT 1-3 | 5.49E−10 | 6.33E+05 | 3.48E−04 |
| WT 1-14 | 7.49E−10 | 5.32E+05 | 3.98E−04 |
| WT 1-29 | 1.23E−09 | 8.96E+04 | 1.10E−04 |
| WT 1-50 | 7.02E−10 | 6.96E+05 | 4.89E−04 |

From Table 5 and Table 6, the above-mentioned mutation sites have little correlation with other sites, provided that the antibody activity is guaranteed.

Finally, it should be noted that the above embodiments are only used for illustration, but not to limit, the technical solutions of the present disclosure. Although the present disclosure has been described in detail with reference to the foregoing embodiments, those of ordinary skill in the art should understand that it is still possible to modify the technical solutions described in the foregoing embodiments, or equivalently replace some or all of the technical features; however, these modifications or replacements do not cause the essence of the corresponding technical solutions to depart from the scope of the technical solutions of the embodiments of the present disclosure.

INDUSTRIAL APPLICABILITY

The isolated binding protein comprising an antigen-binding domain that binds to cardiac troponin I provided in the present disclosure includes specific heavy chain CDRs and light chain CDRs. The binding protein can specifically recognize and bind to the cardiac troponin I and has high sensitivity and specificity. In particular, the binding protein has high affinity for human cTnI protein, and thus, enabling the detection and diagnosis of a disease related to cardiac troponin I.

What is claimed is:

1. An isolated binding protein comprising an antigen-binding domain, wherein the antigen-binding domain comprises six complementarity determining regions of the following amino acid sequences, and has an affinity for cardiac troponin I:
   a complementarity determining region CDR-VH1 having a sequence of G-F-N-X1-K-X2-Y-X3-M-H (SEQ ID NO: 23), where
   X1 is L or I, X2 is D, and X3 is F or Y;
   a complementarity determining region CDR-VH2 having a sequence of R-I-X1-P-E-D-X2-E-T-X3-Y-A-P-E (SEQ ID NO: 24), where X1 is D, X2 is A or G, and X3 is R or K;
   a complementarity determining region CDR-VH3 having a sequence of Y-Y-X1-S-Y-X2-P-F-V-Y (SEQ ID NO:25), where
   X1 is S, and X2 is I, L or V;
   a complementarity determining region CDR-VL1 having a sequence of Q-S-X1-X2-Y-S-N-X3-H-T-Y (SEQ ID NO:26), where
   X1 is I or L, X2 is I or L, and X3 is R;
   a complementarity determining region CDR-VL2 having a sequence of Q-X1-S-X2-R-F-S (SEQ ID NO: 27), where X1 is I, L or V, and X2 is N; and
   a complementarity determining region CDR-VL3 having a sequence of S-X1-S-T-H-X2-P-X3-T (SEQ ID NO: 28), where
   X1 is Q, X2 is L or I, and X3 is F or Y, and
wherein the mutation site of each of the complementarity determining regions is selected from any one of the following mutation combinations:

| Site | CDR-VH1 X1/X3 | CDR-VH2 X2/X3 | CDR-VH3 X2 | CDR-VL1 X1/X2 | CDR-VL2 X1 | CDR-VL3 X2/X3 |
|---|---|---|---|---|---|---|
| Mutation combination 1 | L/F | A/R | I | I/I | I | L/F |
| Mutation combination 2 | L/Y | A/K | L | I/L | L | L/Y |
| Mutation combination 3 | I/F | G/R | V | L/I | V | I/F |
| Mutation combination 4 | I/Y | G/K | L | L/L | L | I/Y |
| Mutation combination 5 | L/F | A/K | V | L/L | V | L/F |
| Mutation combination 6 | L/Y | G/R | I | I/I | I | I/F |
| Mutation combination 7 | I/F | G/K | V | I/L | V | I/Y |
| Mutation combination 8 | I/Y | A/R | I | L/I | I | L/Y |
| Mutation combination 9 | L/F | G/R | L | L/I | L | L/F |
| Mutation combination 10 | L/Y | G/K | I | L/L | I | I/Y |
| Mutation combination 11 | I/F | A/R | L | I/I | L | L/Y |
| Mutation combination 12 | I/Y | A/K | V | I/L | V | I/F |
| Mutation combination 13 | L/F | G/K | L | I/L | L | L/Y |
| Mutation combination 14 | L/Y | A/R | V | L/I | V | L/F |
| Mutation combination 15 | I/F | A/K | I | L/L | I | I/F |
| Mutation combination 16 | I/Y | G/R | V | I/I | V | I/Y |
| Mutation combination 17 | L/F | A/R | I | L/L | I | L/Y |
| Mutation combination 18 | L/Y | A/R | L | I/I | L | I/Y |
| Mutation combination 19 | I/F | A/K | I | I/L | I | L/F |
| Mutation combination 20 | I/Y | G/R | L | L/I | L | I/F |
| Mutation combination 21 | L/F | G/K | V | L/I | V | I/F |
| Mutation combination 22 | L/Y | A/K | L | L/L | L | L/F |
| Mutation combination 23 | I/F | G/R | V | I/I | V | L/Y |
| Mutation combination 24 | I/Y | G/K | I | I/L | I | I/Y |

| Site | CDR-VH1 X1/X3 | CDR-VH2 X2/X3 | CDR-VH3 X2 | CDR-VL1 X1/X2 | CDR-VL2 X1 | CDR-VL3 X2/X3 |
|---|---|---|---|---|---|---|
| Mutation combination 25 | L/F | A/R | V | L/L | V | I/F |
| Mutation combination 26 | L/Y | G/R | I | I/I | I | L/Y |
| Mutation combination 27 | I/F | G/K | L | I/L | L | L/F |
| Mutation combination 28 | I/Y | A/R | I | L/I | I | I/Y |
| Mutation combination 29 | L/F | A/K | L | L/I | L | L/F |
| Mutation combination 30 | L/Y | G/K | V | L/L | V | L/Y |
| Mutation combination 31 | I/F | A/R | L | I/I | L | I/F |
| Mutation combination 32 | I/Y | A/K | V | I/L | V | I/Y |
| Mutation combination 33 | L/F | G/R | I | I/L | I | L/F |
| Mutation combination 34 | L/Y | A/K | V | L/I | V | I/F |
| Mutation combination 35 | I/F | G/K | I | L/L | I | I/Y |
| Mutation combination 36 | I/Y | A/R | L | I/I | L | L/Y |
| Mutation combination 37 | L/Y | G/R | L | I/I | L | I/Y |
| Mutation combination 38 | I/F | G/K | V | I/L | V | L/Y |
| Mutation combination 39 | I/Y | A/K | I | L/I | I | I/F |
| Mutation combination 40 | L/F | G/R | V | LIT | V | L/Y |
| Mutation combination 41 | L/Y | G/K | I | L/L | I | L/F |
| Mutation combination 42 | I/Y | G/R | I | I/L | I | I/Y |
| Mutation combination 43 | L/F | G/K | L | L/L | L | L/Y |
| Mutation combination 44 | L/Y | A/R | V | I/I | V | I/Y |
| Mutation combination 45 | I/F | A/K | L | I/L | L | L/F |
| Mutation combination 46 | I/Y | G/K | V | L/I | V | I/F |
| Mutation combination 47 | L/F | A/R | I | L/I | I | I/F |
| Mutation combination 48 | L/Y | A/K | V | L/L | V | L/F |
| Mutation combination 49 | I/F | G/R | I | I/I | I | L/Y |
| Mutation combination 50 | I/Y | A/R | L | I/L | L | I/Y |
| Mutation combination 51 | L/F | A/K | I | I/L | I | I/F |
| Mutation combination 52 | L/Y | G/R | L | L/I | L | L/Y |
| Mutation combination 53 | I/F | A/R | V | L/L | V | L/F |
| Mutation combination 54 | I/Y | A/K | L | I/I | L | I/Y |

2. The isolated binding protein according to claim 1, wherein the isolated binding protein is one of F(ab')$_2$, Fab', Fab, Fv, scFv, or bispecific antibody.

3. The isolated binding protein according to claim 1, wherein the isolated binding protein comprises a constant region sequence selected from any one of constant region sequences of IgG1, IgG2, IgG3, IgG4, IgA, IgM, IgE, or IgD.

4. The isolated binding protein according to claim 3, wherein the constant region is derived from cattle, horse, dairy cow, pig, sheep, goat, rat, mouse, dog, cat, rabbit, camel, donkey, deer, mink, chicken, duck, goose, turkey, gamecock, or human.

5. The isolated binding protein according to claim 3, wherein the constant region comprises a light chain constant region having a sequence of SEQ ID NO: 9, and a heavy chain constant region having a sequence of SEQ ID NO: 10.

6. The isolated binding protein according to claim 3, wherein the isolated binding protein is labelable with an indicator for showing signal intensity.

7. The isolated binding protein according to claim 1, wherein the antigen-binding domain has an affinity for cardiac troponin I at a $K_D$ value that is less than or equal to $1.41 \times 10^{-9}$ mol/L.

8. The isolated binding protein according to claim 1, wherein the isolated binding protein comprises light chain framework regions FR-L1, FR-L2, FR-L3 and FR-L4 having sequences as set forth in SEQ ID NO: 1 to 4, respectively, and/or heavy chain framework regions FR-H1, FR-H2, FR-H3 and FR-H4 having sequences as set forth in SEQ ID NO: 5 to 8, respectively.

9. An isolated nucleic acid molecule encoding the binding protein according to claim 1, wherein the nucleic acid molecule is DNA or RNA.

10. A vector comprising the nucleic acid molecule according to claim 9.

11. A host cell transformed with the vector according to claim 10.

12. A method for producing the isolated binding protein according to claim 1, comprising
culturing a host cell comprising a nucleic acid encoding the isolated binding protein according to claim 1 in a culture medium under appropriate culture conditions, and recovering the binding protein thus produced in the culture medium or from cultured host cell.

13. A method for detecting cardiac troponin I in a test sample, comprising:
a) contacting the cardiac troponin I in the test sample with the isolated binding protein according to claim 1 under a condition sufficient for the occurrence of antibody binding reaction to form an immune complex; and
b) detecting the presence of the immune complex, the presence of the complex indicating the presence of the cardiac troponin I in the test sample.

14. The method according to claim 13, wherein the test sample is from a human.

15. The method of claim 13, wherein the immune complex comprises a second antibody that binds to the isolated binding protein.

16. The method of claim 13, wherein in step a), the immune complex comprises a second antibody that binds to the cardiac troponin I.

17. A kit comprising the isolated binding protein according to claim 1.

18. A method for diagnosing a disease related to cardiac troponin I, comprising:
A) contacting a sample from a subject with the isolated binding protein according to claim 1 for a binding reaction under a condition sufficient for the occurrence of the binding reaction, and
B) detecting an immune complex produced by the binding reaction, wherein the presence of the immune complex indicates the presence of the disease related to cardiac troponin I.

19. The method according to claim 18, wherein the disease related to cardiac troponin I is cardiovascular disease.

20. The method according to claim 18, wherein the disease related to cardiac troponin I is selected from the group consisting of acute myocardial infarction, acute coronary syndrome, pulmonary infarction, unstable angina, myocardial damage, and a combination thereof.

* * * * *

SEQUENCE LISTING

```
<160> NUMBER OF SEQ ID NOS: 28

<210> SEQ ID NO 1
<211> LENGTH: 26
<212> TYPE: PRT
<213> ORGANISM: Mus musculus

<400> SEQUENCE: 1

Asp Val Val Met Thr Gln Thr Pro Leu Ser Leu Ser Val Ser Leu Gly
1               5                   10                  15

Asp Gln Ala Ser Ile Ser Cys Arg Ser Ser
            20                  25

<210> SEQ ID NO 2
<211> LENGTH: 17
<212> TYPE: PRT
<213> ORGANISM: Mus musculus

<400> SEQUENCE: 2

Leu His Trp Tyr Leu Gln Lys Pro Gly Gln Ser Pro Lys Leu Leu Ile
1               5                   10                  15

Phe

<210> SEQ ID NO 3
<211> LENGTH: 32
<212> TYPE: PRT
<213> ORGANISM: Mus musculus

<400> SEQUENCE: 3

Gly Val Pro Asp Arg Phe Ser Gly Ser Gly Ser Gly Thr Asp Phe Thr
1               5                   10                  15

Leu Lys Ile Asn Arg Val Glu Ala Glu Asp Leu Gly Val Tyr Phe Cys
            20                  25                  30

<210> SEQ ID NO 4
<211> LENGTH: 10
```

```
<212> TYPE: PRT
<213> ORGANISM: Mus musculus

<400> SEQUENCE: 4

Phe Gly Ser Gly Thr Lys Leu Glu Ile Lys
1               5                   10

<210> SEQ ID NO 5
<211> LENGTH: 25
<212> TYPE: PRT
<213> ORGANISM: Mus musculus

<400> SEQUENCE: 5

Glu Val Gln Leu Gln Gln Ser Gly Ala Glu Leu Val Lys Pro Gly Ala
1               5                   10                  15

Ser Val Lys Leu Ser Cys Thr Ala Ser
            20                  25

<210> SEQ ID NO 6
<211> LENGTH: 14
<212> TYPE: PRT
<213> ORGANISM: Mus musculus

<400> SEQUENCE: 6

Trp Met Lys Gln Arg Thr Glu Gln Gly Leu Asp Trp Ile Gly
1               5                   10

<210> SEQ ID NO 7
<211> LENGTH: 35
<212> TYPE: PRT
<213> ORGANISM: Mus musculus

<400> SEQUENCE: 7

Phe Gln Gly Lys Ala Thr Ile Thr Ala Asp Thr Ser Ser Asn Thr Ala
1               5                   10                  15

Tyr Leu Gln Leu Ser Thr Leu Ser Glu Asp Thr Ala Val Tyr Tyr
            20                  25                  30

Cys Ala Arg
        35

<210> SEQ ID NO 8
<211> LENGTH: 11
<212> TYPE: PRT
<213> ORGANISM: Mus musculus

<400> SEQUENCE: 8

Trp Gly Gln Gly Thr Leu Val Thr Ala Ser Ala
1               5                   10

<210> SEQ ID NO 9
<211> LENGTH: 107
<212> TYPE: PRT
<213> ORGANISM: Mus musculus

<400> SEQUENCE: 9

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
```

```
                     50                  55                  60
Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                 85                  90                  95

Pro Ile Val Lys Ser Phe Asn Arg Asn Glu Cys
            100                 105

<210> SEQ ID NO 10
<211> LENGTH: 323
<212> TYPE: PRT
<213> ORGANISM: Mus musculus

<400> SEQUENCE: 10

Ala Lys Thr Thr Pro Pro Ser Val Tyr Pro Leu Ala Pro Gly Ser Ala
 1               5                  10                  15

Ala Gln Thr Asn Ser Met Val Thr Leu Gly Cys Leu Val Lys Gly Tyr
             20                  25                  30

Phe Pro Glu Pro Val Thr Val Thr Trp Asn Ser Gly Ser Leu Ser Ser
         35                  40                  45

Gly Val His Thr Phe Pro Ala Val Leu Gln Ser Asp Leu Tyr Thr Leu
 50                  55                  60

Ser Ser Ser Val Thr Val Pro Ser Ser Thr Trp Pro Ser Gln Thr Val
 65                  70                  75                  80

Thr Cys Asn Val Ala His Pro Ala Ser Ser Thr Lys Val Asp Lys Lys
             85                  90                  95

Ile Val Pro Arg Asp Cys Gly Cys Lys Pro Cys Ile Cys Thr Val Pro
        100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Lys Pro Arg Glu Glu Gln Ile Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asn Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320
```

Ser Pro Gly

<210> SEQ ID NO 11
<211> LENGTH: 219
<212> TYPE: PRT
<213> ORGANISM: Artificial Sequence
<220> FEATURE:
<223> OTHER INFORMATION: Light chain

<400> SEQUENCE: 11

Asp Val Val Met Thr Gln Thr Pro Leu Ser Leu Ser Val Ser Leu Gly
1               5                   10                  15

Asp Gln Ala Ser Ile Ser Cys Arg Ser Ser Gln Ser Ile Ile Tyr Ser
            20                  25                  30

Asn Lys His Thr Tyr Leu His Trp Tyr Leu Gln Lys Pro Gly Gln Ser
        35                  40                  45

Pro Lys Leu Leu Ile Phe Gln Ile Ser Gln Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Asn Ser
                85                  90                  95

Thr His Leu Pro Phe Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 12
<211> LENGTH: 442
<212> TYPE: PRT
<213> ORGANISM: Artificial Sequence
<220> FEATURE:
<223> OTHER INFORMATION: Heavy chain

<400> SEQUENCE: 12

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Leu Lys Glu Tyr
            20                  25                  30

Phe Met His Trp Met Lys Gln Arg Thr Glu Gln Gly Leu Asp Trp Ile
        35                  40                  45

Gly Arg Ile Glu Pro Glu Asp Ala Glu Thr Arg Tyr Ala Pro Glu Phe
    50                  55                  60

Gln Gly Lys Ala Thr Ile Thr Ala Asp Thr Ser Ser Asn Thr Ala Tyr
65                  70                  75                  80

```
Leu Gln Leu Ser Thr Leu Thr Ser Glu Asp Thr Ala Val Tyr Tyr Cys
                85                  90                  95

Ala Arg Tyr Tyr Thr Ser Tyr Ile Pro Phe Val Tyr Trp Gly Gln Gly
            100                 105                 110

Thr Leu Val Thr Ala Ser Ala Ala Lys Thr Thr Pro Pro Ser Val Tyr
            115                 120                 125

Pro Leu Ala Pro Gly Ser Ala Ala Gln Thr Asn Ser Met Val Thr Leu
            130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Gln Thr Val Thr Cys Asn Val Ala His Pro Ala Ser
            195                 200                 205

Ser Thr Lys Val Asp Lys Lys Ile Val Pro Arg Asp Cys Gly Cys Lys
            210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Lys Pro Arg
            275                 280                 285

Glu Glu Gln Ile Asn Ser Thr Phe Arg Ser Val Ser Glu Leu Pro Ile
            290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asn Phe
            355                 360                 365

Phe Pro Glu Asp Ile Thr Val Glu Trp Gln Trp Asn Gly Gln Pro Ala
            370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly
            435                 440

<210> SEQ ID NO 13
<211> LENGTH: 25
<212> TYPE: DNA
<213> ORGANISM: Artificial Sequence
<220> FEATURE:
<223> OTHER INFORMATION: SMARTER II A Oligonucleotide
<220> FEATURE:
<221> NAME/KEY: misc_feature
<222> LOCATION: (25)..(25)
```

<223> OTHER INFORMATION: XXXXX at the 3'-end

<400> SEQUENCE: 13
aagcagtggt atcaacgcag agtac                                                    25

<210> SEQ ID NO 14
<211> LENGTH: 27
<212> TYPE: DNA
<213> ORGANISM: Artificial Sequence
<220> FEATURE:
<223> OTHER INFORMATION: 5'-RACE CDS Primer (5'-CDS)
<220> FEATURE:
<221> NAME/KEY: misc_feature
<222> LOCATION: (26)..(26)
<223> OTHER INFORMATION: v is a, g, or c
<220> FEATURE:
<221> NAME/KEY: misc_feature
<222> LOCATION: (27)..(27)
<223> OTHER INFORMATION: n is a, c, g, or t

<400> SEQUENCE: 14
tttttttttt tttttttttt tttttvn                                                  27

<210> SEQ ID NO 15
<211> LENGTH: 45
<212> TYPE: DNA
<213> ORGANISM: Artificial Sequence
<220> FEATURE:
<223> OTHER INFORMATION: Universal Primer A Mix (UPM)

<400> SEQUENCE: 15
ctaatacgac tcactatagg gcaagcagtg gtatcaacgc agagt                              45

<210> SEQ ID NO 16
<211> LENGTH: 23
<212> TYPE: DNA
<213> ORGANISM: Artificial Sequence
<220> FEATURE:
<223> OTHER INFORMATION: Nested-Universal Primer A (NUP)

<400> SEQUENCE: 16
aagcagtggt atcaacgcag agt                                                      23

<210> SEQ ID NO 17
<211> LENGTH: 33
<212> TYPE: DNA
<213> ORGANISM: Artificial Sequence
<220> FEATURE:
<223> OTHER INFORMATION: mIg-kR

<400> SEQUENCE: 17
ctaacactca ttcctgttga agctcttgac aat                                           33

<210> SEQ ID NO 18
<211> LENGTH: 26
<212> TYPE: DNA
<213> ORGANISM: Artificial Sequence
<220> FEATURE:
<223> OTHER INFORMATION: mIg-HR

<400> SEQUENCE: 18
tcatttacca ggagagtggg agaggc                                                   26

<210> SEQ ID NO 19
<211> LENGTH: 39
<212> TYPE: DNA
<213> ORGANISM: Artificial Sequence

```
<220> FEATURE:
<223> OTHER INFORMATION: cTnI-5G8-HF

<400> SEQUENCE: 19
cccaagctta tggaatgcag ctgtgtcatg ctcttcttc                    39

<210> SEQ ID NO 20
<211> LENGTH: 35
<212> TYPE: DNA
<213> ORGANISM: Artificial Sequence
<220> FEATURE:
<223> OTHER INFORMATION: cTnI-5G8-HR

<400> SEQUENCE: 20
cccgaattct catttaccag gagagtggga gaggc                        35

<210> SEQ ID NO 21
<211> LENGTH: 34
<212> TYPE: DNA
<213> ORGANISM: Artificial Sequence
<220> FEATURE:
<223> OTHER INFORMATION: cTnI-5G8-LF

<400> SEQUENCE: 21
cccaagctta tgaagttgcc tgttaggctg ttgg                         34

<210> SEQ ID NO 22
<211> LENGTH: 41
<212> TYPE: DNA
<213> ORGANISM: Artificial Sequence
<220> FEATURE:
<223> OTHER INFORMATION: cTnI-5G8-LR

<400> SEQUENCE: 22
cccgaattcc taacactcat tcctgttgaa gctcttgaca a                 41

<210> SEQ ID NO 23
<211> LENGTH: 10
<212> TYPE: PRT
<213> ORGANISM: Artificial Sequence
<220> FEATURE:
<223> OTHER INFORMATION: a complementarity determining region CDR-VH1
<220> FEATURE:
<221> NAME/KEY: MISC_FEATURE
<222> LOCATION: (4)..(4)
<223> OTHER INFORMATION: Xaa is L or I
<220> FEATURE:
<221> NAME/KEY: MISC_FEATURE
<222> LOCATION: (6)..(6)
<223> OTHER INFORMATION: Xaa is D or E
<220> FEATURE:
<221> NAME/KEY: MISC_FEATURE
<222> LOCATION: (8)..(8)
<223> OTHER INFORMATION: Xaa is F or Y

<400> SEQUENCE: 23

Gly Phe Asn Xaa Lys Xaa Tyr Xaa Met His
1               5                   10

<210> SEQ ID NO 24
<211> LENGTH: 14
<212> TYPE: PRT
<213> ORGANISM: Artificial Sequence
<220> FEATURE:
<223> OTHER INFORMATION: a complementarity determining region CDR-VH2
<220> FEATURE:
<221> NAME/KEY: MISC_FEATURE
<222> LOCATION: (3)..(3)
<223> OTHER INFORMATION: Xaa is E or D
```

```
<220> FEATURE:
<221> NAME/KEY: MISC_FEATURE
<222> LOCATION: (7)..(7)
<223> OTHER INFORMATION: Xaa is A or G
<220> FEATURE:
<221> NAME/KEY: MISC_FEATURE
<222> LOCATION: (10)..(10)
<223> OTHER INFORMATION: Xaa is R or K

<400> SEQUENCE: 24

Arg Ile Xaa Pro Glu Asp Xaa Glu Thr Xaa Tyr Ala Pro Glu
1               5                   10

<210> SEQ ID NO 25
<211> LENGTH: 10
<212> TYPE: PRT
<213> ORGANISM: Artificial Sequence
<220> FEATURE:
<223> OTHER INFORMATION: a complementarity determining region CDR-VH3
<220> FEATURE:
<221> NAME/KEY: MISC_FEATURE
<222> LOCATION: (3)..(3)
<223> OTHER INFORMATION: Xaa is T or S
<220> FEATURE:
<221> NAME/KEY: MISC_FEATURE
<222> LOCATION: (6)..(6)
<223> OTHER INFORMATION: Xaa is I, L or V

<400> SEQUENCE: 25

Tyr Tyr Xaa Ser Tyr Xaa Pro Phe Val Tyr
1               5                   10

<210> SEQ ID NO 26
<211> LENGTH: 11
<212> TYPE: PRT
<213> ORGANISM: Artificial Sequence
<220> FEATURE:
<223> OTHER INFORMATION: a complementarity determining region CDR-VL1
<220> FEATURE:
<221> NAME/KEY: MISC_FEATURE
<222> LOCATION: (3)..(3)
<223> OTHER INFORMATION: Xaa is I or L
<220> FEATURE:
<221> NAME/KEY: MISC_FEATURE
<222> LOCATION: (4)..(4)
<223> OTHER INFORMATION: Xaa is I or L
<220> FEATURE:
<221> NAME/KEY: MISC_FEATURE
<222> LOCATION: (8)..(8)
<223> OTHER INFORMATION: Xaa is R or K

<400> SEQUENCE: 26

Gln Ser Xaa Xaa Tyr Ser Asn Xaa His Thr Tyr
1               5                   10

<210> SEQ ID NO 27
<211> LENGTH: 7
<212> TYPE: PRT
<213> ORGANISM: Artificial Sequence
<220> FEATURE:
<223> OTHER INFORMATION: a complementarity determining region CDR-VL2
<220> FEATURE:
<221> NAME/KEY: MISC_FEATURE
<222> LOCATION: (2)..(2)
<223> OTHER INFORMATION: Xaa is I, L or V
<220> FEATURE:
<221> NAME/KEY: MISC_FEATURE
<222> LOCATION: (4)..(4)
<223> OTHER INFORMATION: Xaa is N or Q

<400> SEQUENCE: 27

Gln Xaa Ser Xaa Arg Phe Ser
```

```
<210> SEQ ID NO 28
<211> LENGTH: 9
<212> TYPE: PRT
<213> ORGANISM: Artificial Sequence
<220> FEATURE:
<223> OTHER INFORMATION: a complementarity determining region CDR-VL3
<220> FEATURE:
<221> NAME/KEY: MISC_FEATURE
<222> LOCATION: (2)..(2)
<223> OTHER INFORMATION: Xaa is Q or N
<220> FEATURE:
<221> NAME/KEY: MISC_FEATURE
<222> LOCATION: (6)..(6)
<223> OTHER INFORMATION: Xaa is L or I
<220> FEATURE:
<221> NAME/KEY: MISC_FEATURE
<222> LOCATION: (8)..(8)
<223> OTHER INFORMATION: Xaa is F or Y

<400> SEQUENCE: 28

Ser Xaa Ser Thr His Xaa Pro Xaa Thr
1               5
```